United States Patent

Nozaki et al.

[11] Patent Number: 6,040,911
[45] Date of Patent: Mar. 21, 2000

[54] REFERENCE IMAGE FORMING METHOD AND PATTERN INSPECTION APPARATUS

[75] Inventors: Takeo Nozaki, Tokyo; Satoshi Nishii, Kanagawa, both of Japan

[73] Assignee: NEC Corporation, Tokyo, Japan

[21] Appl. No.: 09/141,364

[22] Filed: Aug. 27, 1998

[30] Foreign Application Priority Data

Aug. 29, 1997 [JP] Japan ................................ 9-234018

[51] Int. Cl.[7] .................................................. G01B 11/00
[52] U.S. Cl. ............................................ 356/394; 382/144
[58] Field of Search ............................. 356/394; 382/144, 382/141, 145, 146, 147, 148, 149, 151, 152

[56] References Cited

U.S. PATENT DOCUMENTS

| | | | |
|---|---|---|---|
| 4,202,631 | 5/1980 | Uchiyama et al. | 356/394 |
| 5,307,421 | 4/1994 | Darboux et al. | 382/8 |
| 5,475,766 | 12/1995 | Tsuchiya et al. | 382/144 |

FOREIGN PATENT DOCUMENTS 4-350776  12/1992  Japan .

*Primary Examiner*—Frank G. Font
*Assistant Examiner*—Michael P. Stafira
*Attorney, Agent, or Firm*—Sughrue, Mion, Zinn, Macpeak & Seas, PLLC

[57] ABSTRACT

A reference image forming method is used in a pattern inspection apparatus for scanning a pattern formed on an object to be inspected on the basis of design data with a laser beam having a predetermined wavelength, focusing transmitted light passing through the object on a light-receiving element by using an objective lens, forming a real image from pattern information obtained from the light-receiving element, and comparing the real image with a reference image obtained by imaging the design data, thereby detecting a defect in the object. In this method, reference data is formed by developing the design data as a pattern made of multilevel gradation values on pixels having a resolution higher than an inspection resolution. A reference image is formed by increasing or decreasing the width of each pattern of the reference data as a multilevel gradation pattern with a precision higher than the inspection resolution on the basis of an edge position of a corresponding pattern in the real image. A pattern inspection apparatus is also disclosed.

18 Claims, 6 Drawing Sheets

1 PIXEL=16TIMES PRECISION
8×12=96 (GRADATION VALUE)

| 0 | 0 | 0 | 0 | 0 | 0 | 0 |
|---|---|---|---|---|---|---|
| 128 | 128 | 128 | 128 | 96 | 0 | 0 |
| 255 | 255 | 255 | 255 | 192 | 0 | 0 |
| 255 | 255 | 255 | 255 | 192 | 0 | 0 |
| 255 | 255 | 255 | 255 | 192 | 0 | 0 |
| 255 | 255 | 255 | 255 | 192 | 0 | 0 |
| 255 | 255 | 255 | 255 | 192 | 0 | 0 |

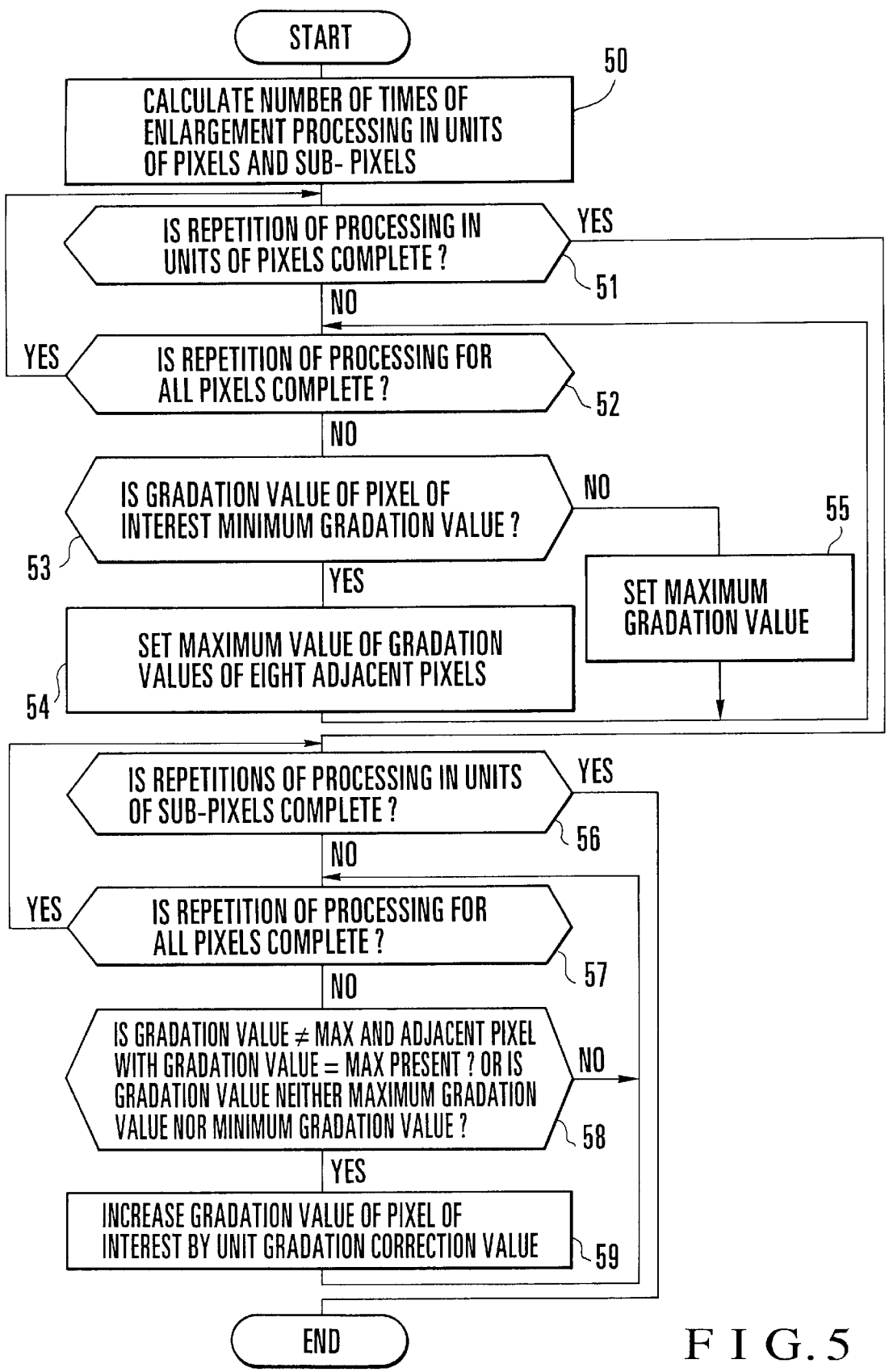
F I G. 5

| 0 | 0 | 0 | 0 | 0 | 0 | 0 |
|---|---|---|---|---|---|---|
| 128 | 0 | 0 | 0 | 0 | 0 | 0 |
| 255 | 128 | 0 | 0 | 0 | 0 | 0 |
| 255 | 255 | 128 | 0 | 0 | 0 | 0 |
| 255 | 255 | 255 | 128 | 0 | 0 | 0 |
| 255 | 255 | 255 | 255 | 128 | 0 | 0 |
| 255 | 255 | 255 | 255 | 255 | 128 | 0 |

FIG. 7

| 255 | 192 | 64 | 0 | 0 | 0 | 0 |
|---|---|---|---|---|---|---|
| 255 | 255 | 192 | 64 | 0 | 0 | 0 |
| 255 | 255 | 255 | 192 | 64 | 0 | 0 |
| 255 | 255 | 255 | 255 | 192 | 64 | 0 |
| 255 | 255 | 255 | 255 | 255 | 192 | 64 |
| 255 | 255 | 255 | 255 | 255 | 255 | 192 |
| 255 | 255 | 255 | 255 | 255 | 255 | 255 |

FIG. 8

| 0 | 0 | 0 | 0 | 0 | 0 | 0 |
|---|---|---|---|---|---|---|
| 0 | 0 | 0 | 0 | 0 | 0 | 0 |
| 0 | 0 | 0 | 0 | 0 | 0 | 0 |
| 64 | 0 | 0 | 0 | 0 | 0 | 0 |
| 191 | 64 | 0 | 0 | 0 | 0 | 0 |
| 255 | 191 | 64 | 0 | 0 | 0 | 0 |
| 255 | 255 | 191 | 64 | 0 | 0 | 0 |

FIG. 9

REFERENCE IMAGE FORMING METHOD AND PATTERN INSPECTION APPARATUS

BACKGROUND OF THE INVENTION

The present invention relates to a pattern inspection apparatus and, more particularly, to a reference image forming method of forming a reference image for a die-to-database inspection from design data, and a pattern inspection apparatus.

In general, a fine pattern such as a semiconductor integrated circuit formed on a photomask, a reticle, a wafer, a liquid crystal member, or the like must be inspected by using a pattern inspection apparatus to check whether the pattern is accurately drawn in accordance with the size and shape of an ideal pattern formed from design data.

First of all, a pattern inspection apparatus of this type converts design data described with the position coordinates of a rectangle or trapezoid and line segment lengths into binary bit data consisting of "0"s and "1"s corresponding to a target pattern (to be inspected).

The apparatus then scans the target pattern with a laser beam and forms a predetermined optical point divergence function from the pattern information obtained by focusing the transmitted light on a light-receiving element or from the edge profile of the pattern image obtained from an image sensing system. The apparatus converts the design data into multilevel gradation data (multilevel data) by using this function and performing convolution processing with the binary bit data, thereby obtaining a reference image.

The apparatus loads the reference image obtained from the design data in synchronism with the real image obtained by scanning performed by the optical system or input from the image sensing system, and detects incoincident points between the images at corresponding pixel positions, thereby detecting defects on the real pattern (die-to-database inspection).

Note that patterns in a real image have dimensional errors with respect to design ideal values, which cause rounding of corners (corner portions), thickening/thinning of lines, and the like, owing to optical conditions and the influences of a manufacturing process, and pseudo defects that are not determined as defects tend to occur due to pseudo errors with respect to the reference image obtained from the design data.

Under the circumstances, therefore, a reference image may be corrected in advance by performing proper edge position detection or feature extraction such as corner recognition in accordance with the feature amount in each inspection area.

In a conventional reference image forming method, when the pattern line width of a reference image is to be corrected, proper edge detection processing is performed for a real image to correct the pattern correction width of the design data in units of binary data and bits (pixels).

In this case, a changed bit pattern is formed from the design bit pattern, and the bit pattern is EX-ORed with the bit data of the target pattern obtained by binarizing the real image, thereby re-sizing each pattern of the reference image.

In addition, a bit-by-bit basis correction template is prepared, which indicates an edge or corner having a predetermined pattern edge angle (e.g., 0°, 45°, 90°, or 135°) with respect to the edge or corner extracted from the design data by edge position detection, corner recognition, or the like.

Subsequently, the correction template that is most similar to the real image corresponding to the edge or corner is selected to correct the original design data, and the corrected design data is converted into multilevel data again to form a reference image. The gradation difference between the obtained reference image and the real image is checked with the threshold of a proper defect algorithm to check whether the target portion is a defect or not. In this manner, defect detection is performed (see, for example, Japanese Patent Laid-Open No. 4-350776).

In such a conventional reference image forming method and pattern inspection apparatus, original design data is corrected by using a correction template similar to the edge or corner of the reference image formed from the design data, thereby forming a reference image again. In this manner, a reference image similar to the real image data of the normal pattern obtained by optical scanning is formed. For this reason, the inspection throughput decreases owing to the correction processing for the design data, and pseudo defects are produced due to the gradation difference from the correction template.

More specifically, in performing pattern correction for design data, a template similar to the shape of a real image is selected from a plurality of templates of pattern shapes represented by bit strings, and a multilevel reference image for comparison is formed by performing convolution processing for a corrected template image and light intensities calculated from the point divergence function obtained by optically scanning the bit strings obtained by logical operation using the selected template. With this processing, with an increase in the number of pixels, the required calculation amount greatly increases, resulting in a decrease in inspection throughput.

In addition, since the enlargement and reduction widths in pattern correction are determined by arithmetic processing for the bit string based on a template within each pixel, the gradation values of the corrected pattern are limited to the gradation distribution of the template.

Furthermore, since gradation correction is executed regardless of the shapes of adjacent patterns, if a pattern edge is not located at a pixel boundary or a corner portion has a rounded portion, the gradation difference between the reference image and the real image obtained by scanning increases. As a result, pseudo defects tend to occur.

For this reason, at the edge portion of a pattern arranged at an arbitrary angle such that the design pattern has an oblique edge, even if gradation correction is performed in units of pixels by using a template, the gradation differences cannot be interpolated.

Since a defect at a pixel boundary or a pattern defect, on an edge, which exhibits poor contrast with respect to the adjacent portions and is smaller than the inspection resolution, in particular, tends to be similar in gradation to the adjacent portions, the defect detection sensitivity based on comparison processing with a reference image deteriorates.

SUMMARY OF THE INVENTION

The present invention has been made to solve the above problems, and has as its object to provide a pattern inspection apparatus which can form a high-precision reference image similar to a real image of an object to be inspected, and can greatly reduce pseudo defects.

In order to achieve the above object, according to the present invention, there is provided a reference image forming method in a pattern inspection apparatus for scanning a pattern formed on an object to be inspected on the basis of design data with a laser beam having a predetermined wavelength, focusing transmitted light passing through the object on a light-receiving element by using an objective lens, forming a real image from pattern information obtained from the light-receiving element, and comparing the real image with a reference image obtained by imaging the design data, thereby detecting a defect in the object, comprising the steps of forming reference data by developing the design data as a pattern made of multilevel gradation values on pixels having a resolution higher than an inspection resolution, and forming a reference image by increasing or decreasing a width of each pattern of the reference data as a multilevel gradation pattern with a precision higher than the inspection resolution on the basis of an edge position of a corresponding pattern in the real image.

BRIEF DESCRIPTION OF THE DRAWINGS

FIG. 5 is a flow chart showing enlargement processing;

FIG. 7 is a view for explaining the reference data of a pattern having a slope of 45°;

FIG. 8 is a view for explaining a pattern after enlargement processing; and

FIG. 9 is a view for explaining a pattern after reduction processing.

DESCRIPTION OF THE PREFERRED EMBODIMENT

The present invention will be described next with reference to the accompanying drawings.

Figure 1:
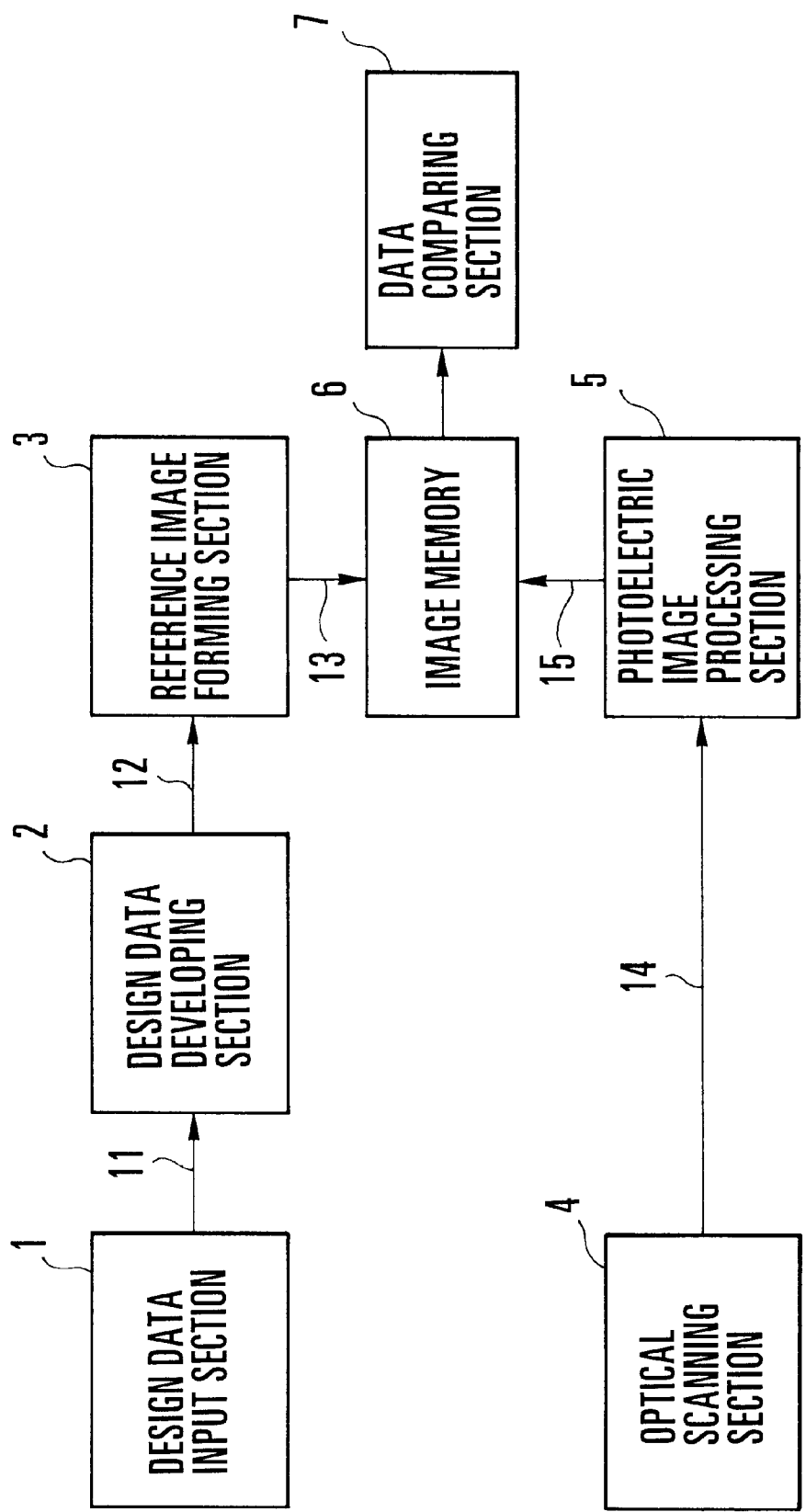
FIG. 1 is a block diagram showing a pattern inspection apparatus according to an embodiment of the present invention.

FIG. 1 shows a pattern inspection apparatus according to an embodiment of the present invention.

This pattern inspection apparatus includes an optical scanning section 4 for outputting a scanning signal 14 by scanning an interconnection pattern to be inspected, i.e., a target pattern, with a laser beam, and a photoelectric image processing section 5 for converting/outputting the scanning signal 14 as a multilevel gradation real image 15.

This apparatus also includes a design data 11 for inputting design data 11 defining the dimensions of a target pattern, a design data developing section 2 for forming multilevel gradation reference data 12 by developing the design data 11 into an interconnection pattern, a reference image forming section 3 for forming a reference image 13 by performing correction to make each interconnection pattern of the reference data 12 similar to the real image 15, and a data comparing section 7 for inspecting the target pattern by comparing the real image 15 of the target pattern, which is obtained by optical scanning, with the reference image 13 formed by the design data 11.

The operation of the present invention will be described next with reference to the accompanying drawings.

The design data 11 described in a format like MEBES is input from the design data input section 1.

The design data developing section 2 then develops the input design data 11 into an interconnection pattern on pixels arranged in the form of a matrix in correspondence with the addresses of the pattern coordinates of the real image 15.

Figure 2:
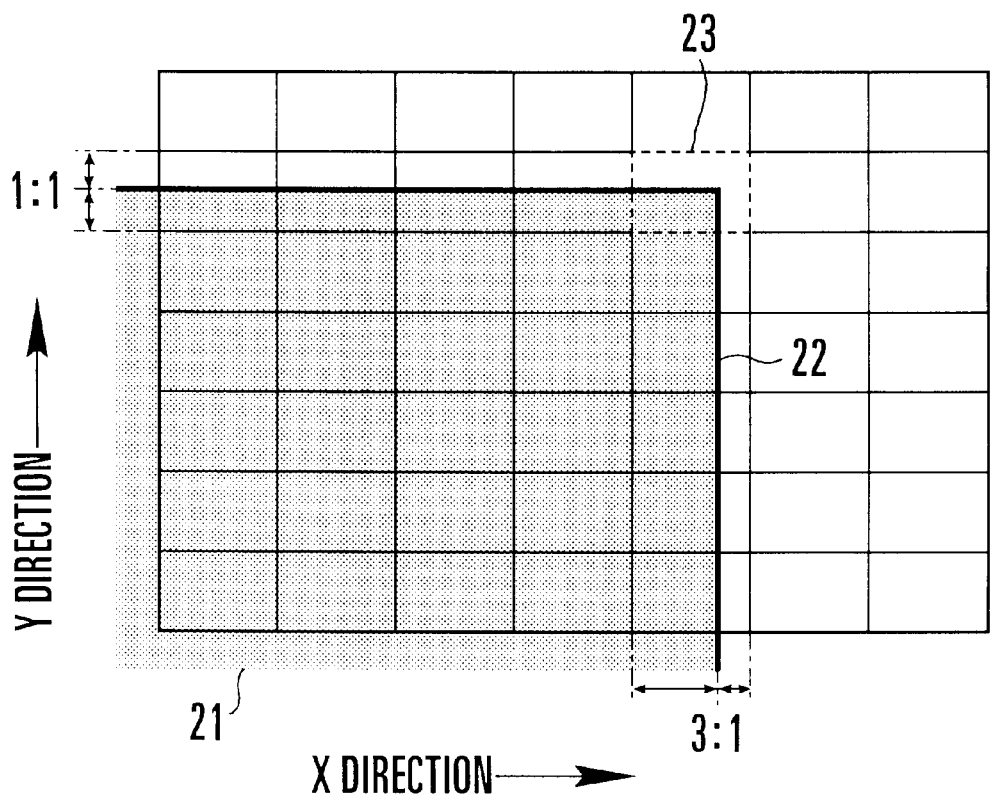
FIG. 2 is a view for explaining part of a developed interconnection pattern.

FIG. 2 shows part of the developed interconnection pattern.

Each pixel corresponds to the developing resolution of the design data developing section 2.

In this case, an edge 22 of a pattern 21 is developed without any discontinuity between pixels. For example, on a pixel 23, the edge 22 is developed at a position corresponding to a ratio of 3:1 in the x direction (horizontal direction), and at a position corresponding to a ratio of 1:1 in the y direction (vertical direction).

A plurality of sub-pixels are set in each pixel to calculate a multilevel gradation value (density value) with a resolution higher than the inspection resolution. The gradation value precision of each pixel is determined by the number of sub-pixels.

If, for example, data is to be developed with a maximum gradation value of 255, a minimum gradation value of 0, and a unit gradation correction value of 1, one pixel is made up of 16×16 sub-pixels, and each sub-pixel takes a binary value of "0" or "1".

Figures 3, 4:
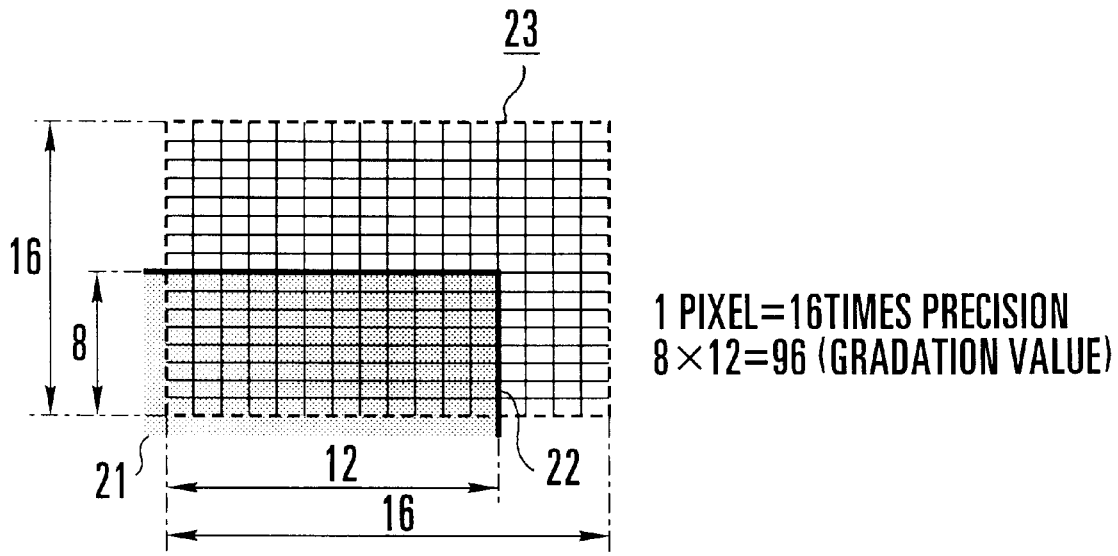
FIG. 3 is an enlarged view of one pixel in FIG. 2.
FIG. 4 is a view for explaining the gradation value of each pixel of the pattern in FIG. 2.

FIG. 3 shows the pixel 23 in FIG. 2. In this case, the pattern 21 is present on 8×12 sub-pixels of the 16×16 sub-pixels.

In this case, if each sub-pixel that belongs to the pattern 21 is represented by "1", and each sub-pixel that does not belong to the pattern 21 is represented by "0", the gradation value of the pixel 23 is 8×12=96.

With this operation, the gradation value of each pixel that does not belong to the pattern 21 becomes the minimum gradation value (MIN=0). Of the pixels belonging to the pattern 21, the pixels other than those corresponding to the pattern edge have the maximum gradation value (MAX= 255).

In addition, each pixel partially belonging to the pattern 21a and corresponding to the pattern edge has a gradation value corresponding to the number of sub-pixels, in the pixel, which belong to the pattern 21.

In this manner, the gradation value of each pixel of the developed pattern 21, i.e., each pattern coordinate address of the real image 15, can be calculated by integrating the area represented by the bit string in each pixel, as shown in FIG. 4.

The design data developing section 2 therefore develops an interconnection pattern on the respective pixels on the basis of the design data 11, and then performs bit integration in units of pixels, thereby calculating a gradation value as a multiple of the unit gradation correction value. The design data developing section 2 outputs the resultant data as the reference data 12.

The reference image forming section 3 increases or decreases the width of each interconnection pattern of the reference data 12 output from the design data developing section 2 to move/correct the edge position of each interconnection pattern, thereby forming the reference image 13 similar to the real image 15.

Note that the correction width is determined on the basis of an address indicating the position of the edge portion of a target pattern of the real image 15 stored in an image memory 6, i.e., the edge address.

Figure 6:
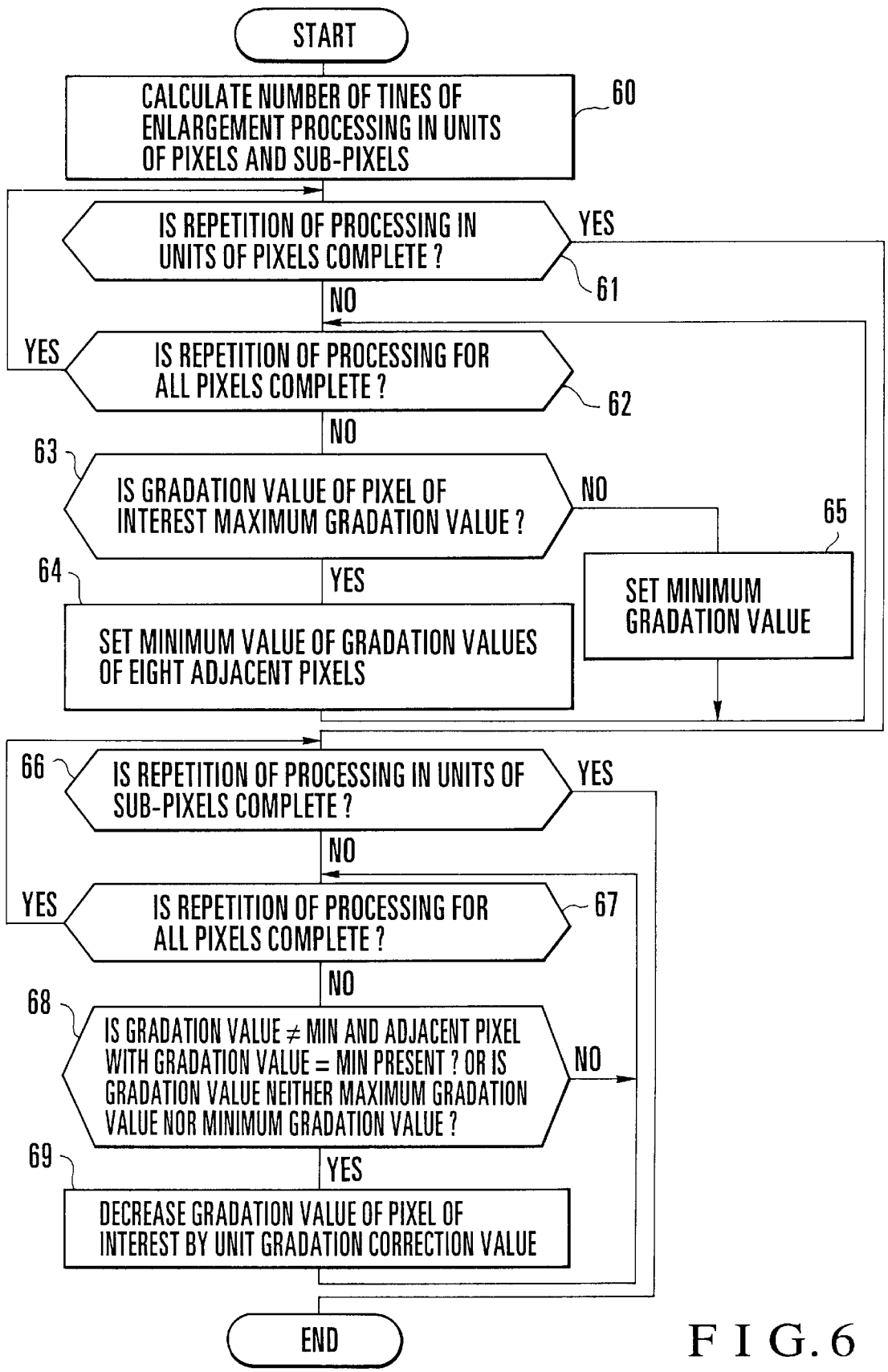
FIG. 6 is a flow chart showing reduction processing.

FIG. 5 shows pattern enlargement processing. FIG. 6 shows pattern reduction processing.

Since both the enlargement processing and the reduction processing are identical in terms of the basic flow of processing, the enlargement processing will be described in detail below with reference to FIG. 5.

Note that the pattern positions of the real image 15 and the reference data 12 are compared in advance to determine whether the target pattern is to be enlarged or reduced.

First of all, an enlargement correction width for an arbitrary target pattern is determined on the basis of the address of an edge of the corresponding pattern obtained from the real image 15 (step 50).

In this case, first of all, the number of gradation levels per pixel is obtained by $$\text{number of gradation levels per pixel} = (\text{maximum gradation value MAX} - \text{minimum gradation value MIN})/(\text{unit gradation correction value}) \quad (1)$$

Note that the unit gradation correction value (the gradation correction width per step) is a gradation addition/subtraction value to be added (subtracted) so as to enlarge (or reduce) the multilevel reference data 12 obtained by developing the design data 11 in units of sub-pixels. This unit gradation correction value must be a submultiple of the value obtained by subtracting the minimum gradation value MIN from the maximum gradation value MAX.

The number of gradation levels per pixel indicates the maximum number of gradation values that can be taken when the unit gradation correction value is the gradation difference.

Assume that the maximum gradation value is 255, the minimum gradation value 0, and the unit gradation correction value 17. In this case, to move an edge of data, all pixels of which are multiples of 17, by one pixel, enlargement (reduction) processing in units of sub-pixels may be performed by $(255-0)/17=15$ times, i.e., the number of times corresponding to the number of gradation levels per pixel.

If therefore, an enlargement correction width is calculated from the edge position of the target pattern of the reference data 12 and the edge position of the corresponding real image 15, the number of times enlargement processing is repeated to move the data by this enlargement correction width can be obtained as follows.

$$\text{number of times of enlargement (reduction) processing per pixel} = \text{quotient of (number of gradation levels corresponding to pattern correction width/number of gradation levels per pixel)} \quad (2)$$

$$= \text{remainder of (number of gradation levels corresponding to pattern correction width/number of gradation levels per pixel)} \quad (3)$$

Enlargement processing (steps 53 to 55) is repeatedly executed for each pixel of the target pattern of the reference data 12 (step 52) by the number of times obtained according to equation (2) in the pixel unit (step 51).

In this enlargement processing, if the pixel of interest has the minimum gradation value (YES in step 53), the gradation value of the pixel of interest is replaced with the maximum gradation value of the gradation values of eight adjacent pixels around (upper, lower, left, right, and oblique positions) the pixel of interest (step 54). If the gradation value of the pixel of interest is not the minimum gradation value (NO in step 53), the gradation value of the pixel of interest is replaced with the maximum gradation value (step 55).

Enlargement processing (steps 58 and 59) is executed for all the pixels of the image obtained in steps 51 to 55 (step 57) by the number of times obtained according to equation (3) in units of sub-pixels (step 56).

In step 58, it is checked on the basis of the following rule whether a pixel of interest is a pixel to be subjected to enlargement processing.

If the gradation value of the pixel of interest is not the maximum gradation value (MAX) and one of the eight adjacent pixels has the maximum gradation value (MAX) or the gradation value of the pixel of interest is neither the maximum gradation value nor the minimum gradation value (YES in step 58), only a gradation value corresponding to the unit gradation correction value is added to the gradation value of the pixel of interest (step 59).

In reduction processing (see FIG. 6), if the gradation value of the pixel of interest is not the minimum gradation value (MIN) and one of the eight adjacent pixels has the minimum gradation value (MIN) or the gradation value of the pixel of interest is neither the maximum gradation value nor the minimum gradation value (YES in step 68), only a gradation value corresponding to the unit gradation correction value is subtracted from the gradation value of the pixel of interest (step 69).

FIG. 7 explains the reference data of a pattern having a slope of 45°.

This pattern has no edge present in a non-pixel portion. The values in FIG. 7 represent the gradation values at the respective pixel positions.

When enlargement processing (see FIG. 5) is performed for this pattern by an amount of 1.25 pixels, a pattern like the one shown in FIG. 8 is obtained.

When reduction processing (see FIG. 6) is performed for the pattern in FIG. 7 by an amount of 1.25 pixels, a pattern like the one shown in FIG. 9 is obtained.

In this manner, the reference image forming section 3 (FIG. 1) performs enlargement or reduction processing for input reference data in units of pixels or sub-pixels to form the reference image 13 similar to the real image 15.

Subsequently, the reference image 13 is stored in the image memory 6 and compared with the already stored real image 15 by the data comparing section 7 to inspect whether the target pattern is accurately drawn on the basis of the dimensions and shape of an ideal pattern formed from the design data.

As has been described above, according to the present invention, the gradation values of the pixels of design data are expressed in a multilevel gradation value matrix with a precision of a multiple. Even if, therefore, a pattern edge of the design data is present in a pixel instead of a discontinuity between the pixels, the gradation at the edge position of the design pattern can be accurately expressed, and a high-precision reference image similar to a real image obtained from a target pattern can be formed.

In addition, since the gradation values after correction are not limited by the gradation distribution of a template unlike the prior art, a high-precision reference image can be formed in accordance with the edge position of the real image.

Since enlargement or reduction processing is also performed in units of pixels in accordance with a pattern correction width, the processing time can be greatly shortened as compared with a case wherein enlargement or reduction processing is performed in units of sub-pixels.

Furthermore, by adjusting the unit gradation correction value, a reference image corresponding to a desired inspection precision can be obtained.

Moreover, pixels subjected to enlargement/reduction processing are identified in units of sub-pixels, and gradation correction is performed in the unit gradation correction value with a resolution higher than a pixel resolution regardless of the angle of an interconnection pattern of design data. Therefore, pattern deformation due to enlargement/reduction processing can be greatly suppressed. Even if the arrangement of design data does not depend on the beam scanning direction, a reference image pattern similar to a real image of a target pattern can be formed.

What is claimed is:

1. A reference image forming method in a pattern inspection apparatus for scanning a pattern formed on an object to be inspected on the basis of design data with a laser beam having a predetermined wavelength, focusing transmitted light passing through the object on a light-receiving element by using an objective lens, forming a real image from pattern information obtained from said light-receiving element, and comparing the real image with a reference image obtained by imaging the design data, thereby detecting a defect in the object, comprising the steps of:

forming reference data by developing the design data as a pattern made of multilevel gradation values on pixels having a resolution higher than an inspection resolution; and forming a reference image by increasing or decreasing a width of each pattern of the reference data as a multilevel gradation pattern with a precision higher than the inspection resolution on the basis of an edge position of a corresponding pattern in the real image.

2. A method according to claim 1, further comprising the steps of:

setting sub-pixels in each pixel to divide the pixel in the form of a matrix; and calculating a gradation value of each pixel on the basis of the number of sub-pixels belonging to a pattern developed in each pixel.

3. A method according to claim 2, further comprising the step of setting a gradation value of a pixel, all sub-pixels of which do not belong to the pattern, as a minimum gradation value, and setting a gradation value of a pixel, all sub-pixels of which belong to the pattern, as a maximum gradation value.

4. A method according to claim 3, further comprising the step of increasing or decreasing a width of each pattern of the reference data by repeating correction of a gradation value of each pixel in units of pixels and sub-pixels by the number of times corresponding to a predetermined correction width.

5. A method according to claim 4, further comprising the steps of:

calculating a correction width by which a target pattern is to be enlarged or reduced on the basis of a positional relationship between an edge of the target pattern of the reference data developed on pixels and an edge of a corresponding pattern on the real image;

dividing the number of gradation levels corresponding to the correction width as a multiple of the unit correction value by the number of gradation levels per pixel obtained by dividing a difference between the maximum gradation value and the minimum gradation value by the unit gradation correction value as a submultiple of the difference between the maximum gradation value and the minimum gradation value; and setting the quotient as the number of times gradation value correction is to be repeated in units of pixels, and setting the remainder as the number of times gradation value correction is to be repeated in units of sub-pixels.

6. A method according to claim 5, further comprising the steps of:

when a gradation value of a pixel of interest is the minimum gradation value, setting a gradation value of a pixel, of pixels adjacent to the pixel of interest, which has the largest gradation value as a new gradation value of the pixel of interest, and setting the maximum gradation value as a new gradation value of the pixel of interest when the gradation value of the pixel is not the minimum gradation value, thereby correcting the gradation value of the pixel; and performing enlargement processing in units of pixels by executing correction of the gradation value for each pixel of the target pattern.

7. A method according to claim 5, further comprising the steps of:

when the gradation value of the pixel of interest is neither the maximum gradation value nor the minimum gradation value or the gradation value of the pixel is not the maximum gradation value and one of pixels around the pixel of interest has the maximum gradation value, increasing the gradation value of the pixel of interest by the unit gradation correction value, thereby correcting the gradation value; and performing enlargement processing in units of sub-pixels by executing correction of the gradation value for each pixel of the target pattern.

8. A method according to claim 5, further comprising the steps of:

when the gradation value of the pixel of interest is the maximum gradation value, setting a gradation value of a pixel, of pixels adjacent to the pixel of interest, which has the minimum gradation value as a new gradation value of the pixel of interest, and setting the minimum gradation value as a new gradation value of the pixel of interest when the gradation value of the pixel is not the maximum gradation value, thereby correcting the gradation value of the pixel of interest; and performing reduction processing in units of pixels by executing correction of the gradation value for each pixel of the target pattern.

9. A method according to claim 5, further comprising the steps of:

when the gradation value of the pixel of interest is neither the maximum gradation value nor the minimum gradation value or the gradation value of the pixel is not the minimum gradation value and one of pixels around the pixel of interest has the minimum gradation value, correcting the gradation value of the pixel of interest by decreasing the gradation value by the unit gradation correction value; and performing reduction processing in units of sub-pixels by executing correction of the gradation value for each pixel of the target pattern.

10. A pattern inspection apparatus for scanning a pattern formed on an object to be inspected on the basis of design data with a laser beam having a predetermined wavelength, focusing transmitted light passing through the object on a light-receiving element by using an objective lens, forming a real image from pattern information obtained from said light-receiving element, and comparing the real image with a reference image obtained by imaging the design data, thereby detecting a defect in the object, comprising:

reference data forming means for forming reference data by developing the design data as a pattern made of multilevel gradation values on pixels having a resolution higher than an inspection resolution; and reference image forming means for forming a reference image by increasing or decreasing a width of each pattern of the reference data as a multilevel gradation pattern with a precision higher than the inspection resolution on the basis of an edge position of a corresponding pattern in the real image.

11. An apparatus according to claim 10, wherein said reference data forming means comprises means for setting sub-pixels in each pixel to divide the pixel in the form of a matrix, and calculating a gradation value of each pixel on the basis of the number of sub-pixels belonging to a pattern developed in each pixel.

12. An apparatus according to claim 11, wherein said reference data forming means comprises means for setting a gradation value of a pixel, all sub-pixels of which do not belong to the pattern, as a minimum gradation value, and setting a gradation value of a pixel, all sub-pixels of which belong to the pattern, as a maximum gradation value.

13. An apparatus according to claim 12, wherein said reference image forming means comprises means for increasing or decreasing a width of each pattern of the reference data by repeating correction of a gradation value of each pixel in units of pixels and sub-pixels by the number of times corresponding to a predetermined correction width.

14. An apparatus according to claim 13, wherein said reference image forming means comprises:

means for calculating a correction width by which a target pattern is to be enlarged or reduced on the basis of a positional relationship between an edge of the target pattern of the reference data developed on pixels and an edge of a corresponding pattern on the real image;

means for dividing the number of gradation levels corresponding to the correction width as a multiple of the unit correction value by the number of gradation levels per pixel obtained by dividing a difference between the maximum gradation value and the minimum gradation value by the unit gradation correction value as a submultiple of the difference between the maximum gradation value and the minimum gradation value; and means for setting the quotient as the number of times gradation value correction is to be repeated in units of pixels, and setting the remainder as the number of times gradation value correction is to be repeated in units of sub-pixels.

15. An apparatus according to claim 14, wherein said reference image forming means comprises:

means for, when a gradation value of a pixel of interest is the minimum gradation value, setting a gradation value of a pixel, of pixels adjacent to the pixel of interest, which has the largest gradation value as a new gradation value of the pixel of interest, and setting the maximum gradation value as a new gradation value of the pixel of interest when the gradation value of the pixel is not the minimum gradation value, thereby correcting the gradation value of the pixel; and means for performing enlargement processing in units of pixels by executing correction of the gradation value for each pixel of the target pattern.

16. An apparatus according to claim 14, wherein said reference image forming means comprises:

means for, when the gradation value of the pixel of interest is neither the maximum gradation value nor the minimum gradation value or the gradation value of the pixel is not the maximum gradation value and one of pixels around the pixel of interest has the maximum gradation value, increasing the gradation value of the pixel of interest by the unit gradation correction value, thereby correcting the gradation value; and means for performing enlargement processing in units of sub-pixels by executing correction of the gradation value for each pixel of the target pattern.

17. An apparatus according to claim 14, wherein said reference image forming means comprises:

means for, when the gradation value of the pixel of interest is the maximum gradation value, setting a gradation value of a pixel, of pixels adjacent to the pixel of interest, which has the minimum gradation value as a new gradation value of the pixel of interest, and setting the minimum gradation value as a new gradation value of the pixel of interest when the gradation value of the pixel is not the maximum gradation value, thereby correcting the gradation value of the pixel of interest; and means for performing reduction processing in units of pixels by executing correction of the gradation value for each pixel of the target pattern.

18. An apparatus according to claim 14, wherein said reference image forming means comprises:

means for, when the gradation value of the pixel of interest is neither the maximum gradation value nor the minimum gradation value or the gradation value of the pixel is not the minimum gradation value and one of pixels around the pixel of interest has the minimum gradation value, correcting the gradation value of the pixel of interest by decreasing the gradation value by the unit gradation correction value; and means for performing reduction processing in units of sub-pixels by executing correction of the gradation value for each pixel of the target pattern.

* * * * *